US006743439B1

(12) United States Patent
Castillo et al.

(10) Patent No.: US 6,743,439 B1
(45) Date of Patent: Jun. 1, 2004

(54) OPHTHALMIC COMPOSITIONS CONTAINING COPOLYMERS OF SULFONATED STYRENE AND MALEIC ANHYDRIDE

(75) Inventors: Ernesto J. Castillo, Arlington, TX (US); Wesley Wehsin Han, Arlington, TX (US); Huixiang Zhang, Fort Worth, TX (US); Ronald F. Berry, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 71 days.

(21) Appl. No.: 10/163,114

(22) Filed: Jun. 5, 2002

Related U.S. Application Data

(60) Provisional application No. 60/301,569, filed on Jun. 27, 2001.

(51) Int. Cl.$^7$ .................................................. A61F 2/00
(52) U.S. Cl. ...................... 424/427; 424/422; 424/423; 424/434; 424/437; 424/484; 424/486; 514/772.1
(58) Field of Search ................................ 424/427, 422, 424/423, 434, 437, 484, 486; 514/772.1

(56) References Cited

U.S. PATENT DOCUMENTS

| 4,362,713 A | 12/1982 | Buck ........................... 424/54 |
| 4,450,261 A | 5/1984 | Chiao et al. ................. 526/214 |
| 4,640,793 A | 2/1987 | Persinski et al. ............. 252/82 |
| 4,911,920 A | 3/1990 | Jani et al. ..................... 424/78 |
| 5,015,467 A | 5/1991 | Smitherman .................. 424/52 |
| 5,679,336 A | 10/1997 | Ali et al. ................. 424/78.04 |
| 5,885,605 A | 3/1999 | Levy .......................... 424/405 |
| 5,889,088 A | 3/1999 | Kisuno et al. .............. 523/205 |

FOREIGN PATENT DOCUMENTS

| EP | 0 860 213 A2 | 8/1998 |
| EP | 0 894 504 A2 | 2/1999 |
| JP | 10319358 | 12/1998 |
| WO | WO 93/05816 | * 4/1993 |
| WO | WO 95/07614 | 3/1995 |
| WO | WO 98/56348 | 12/1998 |

OTHER PUBLICATIONS

Alco Chemical Versa–TL product information, Aug. 14, 2001.

* cited by examiner

*Primary Examiner*—Thurman K. Page
*Assistant Examiner*—Liliana Di Nola-Baron
(74) *Attorney, Agent, or Firm*—Patrick M. Ryan

(57) ABSTRACT

Aqueous pharmaceutical solution compositions preserved with a cationic preservative and comprising a cationic drug and a sulfonated styrene/maleic anhydride copolymer are disclosed. The compositions are particularly well suited for topical ophthalmic use, but may also be used as topically administrable otic or nasal compositions.

10 Claims, No Drawings

OPHTHALMIC COMPOSITIONS CONTAINING COPOLYMERS OF SULFONATED STYRENE AND MALEIC ANHYDRIDE

This application claims priority to U.S. Provisional Application, Ser. No. 60/301,569, filed June 27, 2001.

BACKGROUND OF THE INVENTION

The present invention relates to pharmaceutical compositions comprising a sulfonated styrene/maleic anhydride copolymer. In particular, the present invention relates to comfortable, preserved, topically administrable, aqueous solutions containing a cationic drug and a sulfonated styrene/maleic anhydride copolymer in an amount sufficient to enhance the comfort and/or solubility of the drug.

Pharmaceutical solution compositions are generally preferred over suspension compositions because they are easier to manufacture and process, and because they generally cause less irritation and foreign body sensation when topically applied to the eye. Surfactants and polymers can be added to compositions containing an insoluble drug in an attempt to increase the drug's solubility. For example, as disclosed in U.S. Pat. No. 5,679,336, polystyrene sulfonic acid polymers can be added to topically administrable compositions containing the ophthalmic antibacterial drug ciprofloxacin in order to permit such compositions to be formulated at approximately neutral pH. Previously, aqueous formulations of ciprofloxacin were formulated at acidic pH (approximately pH 4.5) because ciprofloxacin is not soluble at desired levels in simple aqueous compositions at approximately physiological pH (pH 6.0–7.5). Topically administrable ophthalmic compositions that must be formulated at a pH below 6.0 are generally less comfortable than similar compositions that are formulated at approximately physiological pH.

In some cases, ophthalmic drugs that are sufficiently soluble to be formulated as solutions at physiological pH are nevertheless uncomfortable. U.S. Pat. No. 4,911,920 discloses betaxolol compositions containing a water-insoluble ion exchange resin that enhances comfort and provides some extended drug release relative to similar compositions that do not contain such resins. Betoptic® S is a betaxolol product commercially available from Alcon Laboratories, Inc. that incorporates the ion exchange resin known as Amberlite IRP-69, a sodium poly(styrene-divinyl benzene) sulfonate product commercially available from Rohm & Haas.

Although both approaches mentioned above are successful, neither is ideal. Topically administrable ophthalmic compositions formulated as multi-dose products typically contain an ophthalmically acceptable cationic preservative. Solution compositions that contain water-soluble polystyrene sulfonic acid can be difficult to preserve because the negatively charged polystyrene sulfonic acid polymer interacts with the cationic preservative, reducing the preservative's ability to function as a preservative. Suspension compositions containing a water-insoluble resin to enhance comfort are more difficult to manufacture and process than solution compositions.

SUMMARY OF THE INVENTION

The present invention provides aqueous pharmaceutical solution compositions. The compositions are particularly well suited for topical ophthalmic use, but may also be used as topically administrable otic or nasal compositions. The compositions are preserved with a cationic preservative and comprise a cationic drug and a sulfonated styrene/maleic anhydride copolymer.

Among other factors, the present invention is based on the finding that solution compositions comprising a sulfonated styrene/maleic anhydride copolymer are easier to preserve than similar compositions comprising polystyrene sulfonic acid.

DETAILED DESCRIPTION OF THE INVENTION

Unless indicated otherwise, all component amounts are presented on a % (w/w) basis.

The pharmaceutical compositions of the present invention comprise a cationic drug compound. The compositions of the present invention may comprise any pharmaceutically acceptable drug compound, but preferred are compounds that comprise both a ring structure and an amine functional group. The ring structure in the preferred compounds may be any ring, but is preferably a cydoalkyl or an aromatic ring, with compounds containing benzyl or other aromatic rings being the most preferred. Such preferred compounds include, but are not limited to, betaxolol, levobetaxolol, ciprofloxacin, olopatadine and their pharmaceutically acceptable salts. The compositions of the invention are best suited for drug compounds for which enhanced solubility or comfort is desirable.

Sulfonated styrene/maleic anhydride copolymers (and their salts) are known. See for example, U.S. Pat. No. 4,450,261, the entire contents of which are hereby incorporated by reference in the present specification. Multiple grades of sulfonated styrene/maleic anhydride copolymers are commercially available, including those available as Versa TL-3 (weight average molecular weight=20,000), Rs aqueous solution form Versa TL-4 (25% w/w Versa TL-3), and Versa TL-7 (weight average molecular weight=15,000) from Alco Chemical, a division of National Starch and Chemical Co. (Chattanooga, Tennessee). Generally, the sulfonated styrene/maleic anhydride copolymers suitable for use in the compositions of the present invention will have a molecular weight (weight average) from 5000 to 100,000. The ratio of styrene sulfonic acid to maleic anhydride in the copolymers suitable for use in the compositions of the present invention will range from 2:1–4:1, and will preferably be about 3:1. The compositions of the present invention comprise a sulfonated styrene/maleic anhydride copolymer in an amount effective to enhance the selected drug's solubility or comfort. In general, the amount of sulfonated styrene/maleic anhydride copolymer will range from 0.1 to 10%, preferably 1 to 5%, and most preferably 2 to 4%.

In addition to a drug and a sulfonated styrene/maleic anhydride copolymer, the compositions of the present invention include a cationic preservative such as quatemary ammonium compounds including, but not limited to benzalkonium chloride, benzododecinium bromide, and polyquatemium-1. The amount of preservative to be included in the compositions of the present invention will generally range from 0.001 to 0.03%, preferably 0.001 to 0.015%.

The compositions of the present invention may also include one or more ingredients conventionally found in aqueous ophthalmic, otic or nasal formulations, such as surfactants (e.g., polysorbates, polyethoxylated castor oil derivatives and tyloxapol), viscosity-imparting agents (e.g., carbomer 974P, polyvinyl alcohol or hydroxypropyl methylcellulose), chelating agents (e.g., edetate disodium) and tonicity agents (e.g., sodium chloride, glycerin or mannitol). The compositions will also normally include buffering agents, such as borates, acetates, and phosphates, and pH-adjusting agents, such as NaOH, HCI, and tromethamine, to set and maintain the pH at physiologically acceptable pH (ideally between 6.0 and 7.5). The compositions of the present invention may also contain additional drug compounds.

The following examples are presented to illustrate further certain preferred embodiments of the present invention and should not be interpreted as limiting the scope of the invention in any way.

COMPARATIVE EXAMPLE 1

The following formulations were prepared and then subjected to preservative efficacy testing. The results are shown at the bottom of Table 1. European preservative efficacy standards are more difficult to meet than USP standards. If a formulation passes EP-B (Pharm. Eur. B; minimum European standards), it will also pass USP standards.

TABLE 1

| | | | | | | | | |
|---|---|---|---|---|---|---|---|---|
| Travoprost | 0.004 | 0.004 | 0.004 | 0.004 | 0.004 | 0.004 | 0.004 | 0.004 |
| Levobetaxolol HCl | 0.56 | 0.56 | 0.55 | 0.56 | 0.56 | 0.56 | 0.56 | 0.56 |
| HCO-40 | 0.5 | 0.5 | 0.5 | 0.5 | 0.5 | 0.5 | 0.5 | 0.5 |
| Polystyrene Sulfonic Acid, Sodium Salt | — | — | 1 | 1.5 | — | 1 | 1 | — |
| Amberlite IRP-69 | 1 | 0.75 | — | — | 1 | — | — | 1 |
| Carbomer 974P | 0.35 | 0.2 | — | — | 0.35 | — | — | 0.35 |
| Mannitol | 3.5 | — | 3.5 | 3.5 | 3.3 | 3.7 | 3.7 | 3.3 |
| Glycerin | — | 1.8 | — | — | — | — | — | — |
| N-Lauroyl-sarcosine | 0.05 | 0.05 | 0.05 | 0.04 | 0.05 | 0.05 | 0.05 | 0.04 |
| Boric Acid | 0.3 | 0.35 | 0.3 | 0.35 | 0.3 | 0.3 | 0.3 | 0.3 |
| Edetate Disodium | 0.01 | 0.01 | 0.01 | 0.1 | 0.01 | 0.1 | — | 0.01 |
| Tromethamine | 0.12 | qs pH 6.0 | 0.12 | qs pH 6.0 | qs pH 6.0 | qs pH 6.0 | qs pH 6.0 | qs pH 6.0 |
| Benzalkonium Chloride | 0.015 | 0.01 | 0.015 | 0.04 | 0.015 | 0.015 | — | 0.015 |
| Preservative Efficacy Testing Results | Pass EP-B | Pass EP-B | Fails All | Fails All | Pass USP | Pass USP | Fails All | Pass USP |

EXAMPLE 1

Representative Composition and Compounding Procedure

| INGREDIENT | CONC.(%) |
|---|---|
| Levobetaxolol HCl | 0.56 |
| Versa TL-3 | 1.5 |
| Xanthan Gum | 0.45 |
| Mannitol | 1.9 |
| Boric Acid | 0.4 |
| Edetate Disodium | 0.2 |
| Benzododecinium Bromide | 0.012 |
| N-Lauroylsarcosine | 0.05 |
| Tromethamine | q.s. pH 6.5 |
| Purified Water | q.s. 100 |

Method of Preparation (250 g batch): To a tared Schott bottle, in the order indicated, the batch amounts of the following components were combined:

Versa TL-3 (stir until completely dissolved)

levobetaxolol hydrochloride mannitol boric acid disodium EDTA benzododecinium bromide xanthan gum (added as 1.2% stock solution)

The batch was brought to 240 g by addition of purified water. 2 mL of 20% tromethamine was added. The batch was stirred overnight, after which time the batch amount of N-lauroylsarcosine was added. The batch was adjusted to pH 6.5 by addition of 3.5 mL of 20% tromethamine, and to 250 g by the addition of purified water. The batch was steam sterilized in an autoclave oven at 121° C. for 60 minutes (liquid cycle).

EXAMPLE 2

Representative Composition and Compounding Procedure

| INGREDIENT | CONC.(%) |
|---|---|
| Travoprost | 0.004 |
| Polyoxyl 40 hydrogenated castor oil | 0.5 |
| Levobetaxolol HCl | 0.56 |
| Versa TL-3 | 1.0 |
| Mannitol | 1.9 |
| Boric Acid | 0.4 |
| Edetate Disodium | 0.2 |
| Benzalkonium Chloride | 0.015 |
| N-Lauroylsarcosine | 0.05 |
| Tromethamine | q.s. pH 6.5 |
| Purified Water | q.s. 100 |

Method of Preparation: A stock solution of 0.04% travoprost and 5% polyoxyl 40 hydrogenated castor oil is prepared by combining the batch amounts of each (the surfactant is added as a 10% stock solution) with water sonicating the batch for one hour, and stirring for at least two hours.

In a tared vessel, the batch amounts of the following components were added, in the order indicated.

Versa TL-3 (added to 20% final batch weight of water, and stirred until completely dissolved)

levobetaxolol hydrochloride mannitol boric acid disodium EDTA benzalkonium chloride (added as 0.9991% stock solutin)

The pH is adjusted to 5.5–6.0 by addition of 20% tromethamine solution.

The final batch amount of N-lauroyl sarcosine is added.

The batch is brought to 85% of final weight with water.

Add final batch amounts of travoprost and polyoxyl 40 hydrogenated castor oil are added as the stock solution above.

The batch is adjusted to 99% of final weight by addition of purified water.

The pH is adjusted to 6.5 by addition of 20% tromethamine solution.

The batch is brought to its final weight by addition of purified water.

The batch is sterile filtered through a 0.22 μ cellulose acetate filtration unit

EXAMPLE 3

The Formulations Shown Below Were Prepared.

| INGREDIENT | CONC.(%) | |
|---|---|---|
| FORMULATION | A | B |
| Levobetaxolol HCl | 0.56 | 0.56 |
| Polystyrene Sulfonic Acid, Sodium Salt, 500 KD | 1.5 | — |
| Versa TL-3 | — | 1.5 |
| Xanthan Gum | 0.45 | 0.45 |
| Mannitol | 3.36 | 1.9 |
| Boric Acid | 0.4 | 0.4 |
| Edetate Disodium | 0.16 | 0.2 |
| Benzododecinium Bromide | 0.012 | 0.012 |
| N-lauroylsarcosine | 0.04 | 0.05 |
| Tromethamine/HCl | q.s. pH = 6.5 | q.s. pH = 6.5 |
| Purified Water | q.s. 100 | q.s. 100 |

Formulations A and B were subjected to preservative efficacy testing. The results are shown in Table 2 below.

TABLE 2

| | Log Reduction of Microorganisms After | | | | | |
|---|---|---|---|---|---|---|
| | 6 Hr | | 24 Hr | | Day 7 | |
| Test Organisms | Form. A | Form. B | Form. A | Form. B | Form. A | Form. B |
| S. aureus | 0.5 | 2.9 | 1.6 | 4.9 | 4.3 | 4.9 |
| P. aeruginosa | 1.0 | 5.1 | 0.9 | 5.1 | 0(regrowth) | 5.1 |
| E. coli | 0.3 | 5.0 | 0.4 | 5.0 | 1.7 | 5.0 |
| C. albicans | N/A | N/A | N/A | N/A | 2.2 | 5.0 |
| A. niger | N/A | N/A | N/A | N/A | 1.0 | 1.7 |

| | Log Reduction of Microorganisms After | | | | | |
|---|---|---|---|---|---|---|
| | Day 14 | | Day 21 | | Day 28 | |
| Test Organisms | Form. A | Form. B | Form. A | Form. B | Form. A | Form. B |
| S. aureus | N/A | 4.9 | N/A | 4.9 | N/A | 4.9 |
| P. aeruginosa | N/A | 5.1 | N/A | 5.1 | N/A | 5.1 |
| E. coli | N/A | 5.0 | N/A | 5.0 | N/A | 5.0 |
| C. albicans | N/A | 5.0 | N/A | 5.0 | N/A | 5.0 |
| A. niger | N/A | 1.8 | N/A | 2.6 | N/A | 2.7 |

The results in Table 2 above show that after 7 days Formulation A, containing polystyrene sulfonic acid, failed to meet U.S.P. or Pharm. Eur. B. compendial preservative efficacy standards. Testing after 7 days was cancelled for Formulation A. Formulation B, however, which contained a sulfonated styrene/maleic anhydride copolymer, met preservative efficacy standards for both U.S.P. and Pharm. Eur. B

EXAMPLE 4

The Following Formulations Were Prepared.

| INGREDIENT | CONC.(%) | |
|---|---|---|
| FORMULATION | C | D |
| Levobetaxolol HCl | 0.56 | 0.56 |
| Travoprost | 0.004 | 0.004 |
| Polyoxyl 40 Hydrogenated Castor Oil | 0.5 | 0.5 |
| Versa TL-3 | 1 | — |
| Amberlite IRP 69 | — | 0.75 |
| Xanthan Gum | — | 0.4 |
| Tyloxapol | — | 0.025 |
| Mannitol | 1.9 | 3.7 |
| Boric Acid | 0.4 | 0.35 |
| Edetate Disodium | 0.2 | 0.1 |
| Benzalkonium Chloride | 0.015 | 0.015 |
| N-lauroylsarcosine | 0.05 | 0.06 |
| Tromethamine/HCl | q.s. pH = 6.5 | q.s. pH = 6.0 |
| Purified Water | qs 100% | qs 100% |

Formulations C and D were subjected to abbreviated preservative efficacy testing (i.e., screening). The results are shown in Table 3 below:

TABLE 3

| | Log Reduction of Microorganisms After | | | | | |
|---|---|---|---|---|---|---|
| | 6 Hr | | 24 Hr | | Day 7 | |
| Test Organisms | Form. C | Form. D | Form. C | Form. D | Form. C | Form. D |
| S. aureus | 0.2 | 0.2 | 1.1 | 0.4 | 5.0 | 1.3 |
| P. aeruginosa | 5.0 | 5.0 | 5.0 | 5.0 | 5.0 | 5.1 |
| E. coli | 5.0 | 2.4 | 5.0 | 5.0 | 5.0 | 5.0 |
| C. albicans | N/A | N/A | N/A | N/A | 3.8 | 1.8 |
| A. niger | N/A | N/A | N/A | N/A | 0.9 | 1.8 |

Based on the results shown in Table 3, the formulation of Example C is projected to fail European preservative efficacy standards but to, pass U.S. preservative efficacy standards. In contrast, the formulation of Example D is projected to fail U.S. and European preservative efficacy standards.

EXAMPLE 5

The Following Two Representative Formulations Were Prepared.

| | CONC.(%) | |
|---|---|---|
| INGREDIENT | E | F |
| Travoprost | 0.0015 | 0.0015 |
| Betaxolol HCl | 0.56 | 0.56 |
| Versa TL-3 | 2.5 | 2.5 |
| Polyoxyl 40 Hydrogenated Castor Oil | 0.2 | 0.2 |
| Mannitol | 3.0 | 3.0 |
| Boric acid | 0.45 | 0.45 |
| Edetate disodium | 0.2 | 0.1 |
| Benzalkonium chloride | 0.015 | 0.015 |
| N-lauroylsarcosine | 0.05 | 0.05 |
| Tromethamine/HCl | q.s. pH6.5 | q.s. pH6.5 |
| Purified water | q.s. 100 | q.s. 100 |

Formulations E and F were subjected to abbreviated preservative efficacy testing. The results are shown in Table 4 below.

TABLE 6

| | Log of Initial Counts | | Log Reduction of Microorganism After | | | | | |
| --- | --- | --- | --- | --- | --- | --- | --- | --- |
| | | | 6 Hr | | 24 Hr | | Day 7 | |
| Test Organisms | Form. E | Form. F | Form. E | Form. F | Form. E | Form. F | Form. E | Form. F |
| S. aureus | 6.1 | 6.2 | 0.8 | 1.7 | 3.7 | 5.0 | 5.1 | 5.3 |
| P. aeruginosa | 6.3 | 6.1 | 5.3 | 5.1 | 5.3 | 5.1 | 5.3 | 5.1 |
| E. coli | 6.0 | 6.2 | 4.7 | 5.2 | 5.0 | 5.2 | 5.0 | 5.2 |
| C. albicans | 6.1 | 6.0 | N/A | N/A | N/A | N/A | 5.1 | 5.0 |
| A. niger | 5.5 | 6.1 | N/A | N/A | N/A | N/A | 2.3 | 2.0 |

Both formulations E and F are projected to pass Ph. Eur. B preservative efficacy requirements.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A preserved, aqueous pharmaceutical solution composition suitable for topical ophthalmic, otic or nasal use comprising a cationic drug, a cationic preservative, and a sulfonated styrene/maleic anhydride copolymer, wherein the drug is selected from the group consisting of betaxolol; levobetaxolol; ciprofloxacin; olopatadine; and their pharmaceutically acceptable salts.

2. The composition of claim 1 wherein the sulfonated styrene/inaleic anhydride copolymer has a molecular weight from 5000 to 100,000.

3. The composition of claim 1 wherein the composition comprises from 0.1 to 10% of the sulfonated styrene/maleic anhydride copolymer.

4. The composition of claim 3 wherein the composition comprises from 1 to 5% of the sulfonated styrene/maleic anhydride copolymer.

5. The composition of claim 4 wherein the composition comprises from 2 to 4% of the sulfonated styrene/maleic anhydride copolymer.

6. The composition of claim 1 wherein the cationic preservative is a quatemary ammonium compound.

7. The composition of claim 6 wherein the cationic preservative is selected from the group consisting of benzalkonium chloride; benzododecinium bromide; and polyquatemium-1.

8. The composition of claim 7 wherein the composition comprises from 0.001 to 0.03% of the cationic preservative.

9. The composition of claim 8 wherein the composition comprises from 0.001 to 0.015% of the cationic preservative.

10. The composition of claim 1 wherein the composition is a topically administrable ophthalmic composition.

* * * * *